US012746304B2

(12) United States Patent
Udangawa et al.

(10) Patent No.: US 12,746,304 B2
(45) Date of Patent: Sep. 29, 2026

(54) NANOCOMPOSITE FIBERS WITH A DRAMATIC REDUCTION IN HUMAN PLASMA COAGULATION TIME

(71) Applicant: RENSSELAER POLYTECHNIC INSTITUTE, Troy, NY (US)

(72) Inventors: Ranodhi Nilochani Udangawa, Troy, NY (US); Chiara Diamante Mancinelli, Croton-on-Hudson, NY (US); Caitlyn A. Chapman, Pittsburgh, PA (US); Charles Frederick Willard, Cambridge, MA (US); Trevor John Simmons, Troy, NY (US); Robert John Linhardt, Albany, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 909 days.

(21) Appl. No.: 17/427,288

(22) PCT Filed: Jan. 31, 2020

(86) PCT No.: PCT/US2020/016119

§ 371 (c)(1),
(2) Date: Jul. 30, 2021

(87) PCT Pub. No.: WO2020/160413

PCT Pub. Date: Aug. 6, 2020

(65) Prior Publication Data

US 2022/0111113 A1 Apr. 14, 2022

Related U.S. Application Data

(60) Provisional application No. 62/799,090, filed on Jan. 31, 2019.

(51) Int. Cl.

| | |
|---|---|
| ***A61L 24/00*** | (2006.01) |
| ***D01D 5/00*** | (2006.01) |
| ***D01F 8/02*** | (2006.01) |
| ***D01F 8/18*** | (2006.01) |

(52) U.S. Cl.

CPC .......... *A61L 24/0089* (2013.01); *D01D 5/003* (2013.01); *D01F 8/02* (2013.01); *D01F 8/18* (2013.01); *A61L 2400/04* (2013.01); *A61L 2400/12* (2013.01)

(58) Field of Classification Search

CPC ............. A61L 24/0089; A61L 2400/04; A61L 2400/12; A61L 15/18; A61L 15/28; D01D 5/003; D01F 8/02; D01F 8/18

See application file for complete search history.

(56) References Cited

U.S. PATENT DOCUMENTS

| | | | | |
|---|---|---|---|---|
| 7,192,672 B2 | | 3/2007 | Horichi | |
| 7,828,659 B2 | | 11/2010 | Wada | |
| 8,595,835 B2 | | 11/2013 | Kolton | |
| 8,607,515 B2 | | 12/2013 | Jarvis | |
| 10,137,037 B2 | | 11/2018 | Tout | |
| 11,048,297 B2 | | 6/2021 | Han | |
| 11,137,409 B2 | | 10/2021 | Chapman | |
| 11,267,981 B2 | | 3/2022 | Duncan | |
| 2009/0028915 A1 | | 1/2009 | Code | |
| 2009/0048571 A1 | | 2/2009 | Catalan | |
| 2011/0165811 A1 | * | 7/2011 | Hill | D01D 5/0038 264/465 |
| 2012/0259262 A1 | | 10/2012 | Huey et al. | |
| 2014/0027938 A1 | * | 1/2014 | Swatloski | D01D 5/0046 264/10 |
| 2015/0306274 A1 | | 10/2015 | Hardy et al. | |
| 2016/0106838 A1 | | 4/2016 | Agostino | |

FOREIGN PATENT DOCUMENTS

| | | | | |
|---|---|---|---|---|
| WO | 2012040310 A2 | | 3/2012 | |
| WO | 2012088059 A2 | | 6/2012 | |
| WO | 2015097047 A1 | | 7/2015 | |
| WO | WO-2018169479 A1 | * | 9/2018 | C08B 15/10 |

OTHER PUBLICATIONS

International Search Report and The Written Opinion of the International Searching Authority, International Application No. PCT/US2020/016119, mailed Apr. 23, 2020.

Thakur et al. "Eco friendly polymers nanocomposites" pp. 295-321, (STRUCTMAT, vol. 75), Jun. 2015.

Udangawa et al. "Novel Cellulose—Halloysite Hemostatic Nanocomposite Fibers with a Dramatic Reduction in Human Plasma Coagulation Time". vol. 11, Issue 17, Published Apr. 12, 2019.

Govindasamy et al."Synthesis and Characterisation of Electrospun Chitosan Membranes Reinforced by Halloysite Nanotubes." Journal of Mechanics in Medicine and Biology vol. 14, No. 4 (2014) 1450058 (20 pages).

* cited by examiner

*Primary Examiner* — Snigdha Maewall

(74) *Attorney, Agent, or Firm* — Barclay Damon LLP; Anthony P. Gangemi

(57) ABSTRACT

A method of making a cellulose-nanoclay hemostatic nanocomposite fiber, including the steps of preparing a homogenous cellulose solution including cellulose and a room temperature ionic liquid, preparing a nanoclay suspension including halloysite and distilled water, electrospinning the cellulose solution into a first bath including the nanoclay suspension, transferring solidified cellulose-halloysite fibers from the first bath to a second bath including ethanol and distilled water, removing the solidified cellulose-halloysite fibers from the second bath, and freeze-drying the solidified cellulose-halloysite fibers.

10 Claims, 13 Drawing Sheets

NANOCOMPOSITE FIBERS WITH A DRAMATIC REDUCTION IN HUMAN PLASMA COAGULATION TIME

CROSS REFERENCE TO RELATED APPLICATION(S)

This application claims the benefit of U.S. Provisional Patent Application No. 62/799,090, filed Jan. 31, 2019, which is incorporated by reference as if disclosed herein in its entirety.

FIELD

The present technology relates to nanocomposite fibers and, more particularly, to methods of forming nanocomposite fibers having improved hemostatic qualities.

BACKGROUND

There remains an urgent need in the medical community for the development of hemostatic agents to treat hemorrhage associated with traumatic injuries, surgical procedures, and frequent bleeding events resulting from blood coagulation disorders. Patients suffering from hereditary blood clotting disorders, such as hemophilia and von Willebrand disease, suffer from often unexplained and recurrent internal and external bleeding episodes throughout their lives. These external bleeding episodes include prolonged nosebleeds (epistaxis), bleeding from the gums, and excessive bleeding from small cuts or wounds. Even though many of these episodes are non-life-threatening, they can cause extreme discomfort in such patients. In the case of severe hemorrhage, it is critical to cease bleeding as quickly as possible to prevent imminent death. On a battlefield, most fatalities are due to severe hemorrhage and transpire within the first hour of receiving a wound. Thus, the patient's chance of survival depends on a first responder's ability to minimize blood loss.

There have been a number of topical anti-hemorrhagic agents developed to stop external hemorrhages. Many consist of a polymer or polymer blend mixed with a blood-clotting agent. HemCon, Chitoseal, and Celos represent several commercially available wound dressings that contain the biopolymer chitosan as the hemostatic agent. Most common commercially available hemostatic dressings, including Quikclot Combat Gauze® ("QCG"), are produced either by immersing or spraying the fibrous substrate with a slurry or suspension containing a clotting agent. These products fail to provide prolonged clotting activity because of the loss of clotting agent due to leaching. Extrusion of blends of polymers and clotting agents has also been used to produce hemostatic fibrous materials. However, the clotting agents inside these fibers have minimum or no contact with the external environment making these ineffective in promoting coagulation. Furthermore, the heterogeneous nature of extrusion processes negatively impacts the mechanical properties of these polymeric fiber products.

Naturally occurring aluminosilicate clay is the most popular choice of hemostatic agent used in a wide range of hemostatic wound dressings. Kaolin aluminosilicate clay promotes coagulation by activating factor XII of the coagulation cascade without an accompanying exothermic reaction. In contrast, zeolite clays release thermal energy on contact with the water in blood. This exothermic reaction can cause second-degree burns in patients treated with zeolite-based hemostatic products. Thus, the current generation of clay-based topical hemostatic wound dressings almost exclusively contains kaolin clay. However, kaolin-based hemostatic products quickly lose effectiveness as the water in blood washes away, or leaches, the clotting agent. Therefore, an improved hemostatic agent is needed.

SUMMARY

Accordingly, some embodiments of the present technology are directed to a halloysite nanoclay physically embedded onto the surface of cellulose nanofibers to prevent leaching of the clotting factors and to promote human plasma coagulation. In some embodiments, a halloysite clay hemostatic nanocomposite was fabricated using a one-step wet-wet electrospinning technique and evaluated for human plasma coagulation speed.

According to a first embodiment of the present technology, a method of making a cellulose—nanoclay hemostatic nanocomposite fiber is provided. The method includes the steps of preparing a cellulose solution including cellulose and a non-volatile solvent, preparing a nanoclay suspension including an aluminosilicate and water, electrospinning the cellulose solution into a first bath including the nanoclay suspension, and removing solidified cellulose—nanoclay fibers from the first bath.

In some embodiments, the non-volatile solvent is a room temperature ionic liquid.

In some embodiments, the cellulose solution is homogenous.

In some embodiments, the aluminosilicate is halloysite.

In some embodiments, the nanoclay suspension further includes alcohol.

In some embodiments, the method further includes freeze-drying the solidified cellulose-nanoclay fibers.

In some embodiments, the method further includes transferring the solidified cellulose-nanoclay fibers to a second bath including alcohol and water. In other embodiments, the method further includes removing the solidified cellulose nanoclay fibers from the second bath, and freeze-drying the solidified cellulose—nanoclay fibers.

In some embodiments, the solidified cellulose—nanoclay fibers have an average diameter of about 190 nm to about 710 nm.

In some embodiments, the solidified cellulose—nanoclay fibers are configured to coagulate human plasma in an average time of about 124 seconds to about 162 seconds.

According to another embodiment of the present technology, a method of making a cellulose—nanoclay hemostatic nanocomposite fiber is provided. The method including the steps of preparing a homogenous cellulose solution including cellulose and a room temperature ionic liquid, preparing a nanoclay suspension including halloysite and distilled water, electrospinning the cellulose solution into a first bath including the nanoclay suspension, transferring solidified cellulose—halloysite fibers from the first bath to a second bath including ethanol and distilled water, removing the solidified cellulose—halloysite fibers from the second bath, and freeze-drying the solidified cellulose—halloysite fibers.

In some embodiments, the solidified cellulose—halloysite fibers have an average diameter of about 450 nm.

In some embodiments, the solidified cellulose—halloysite fibers have a specific surface area of about 33.6 $m^2g^{-1}$.

In some embodiments, the solidified cellulose—halloysite fibers are configured to coagulate human plasma in an average time of about 143 seconds.

In some embodiments, a cellulose—nanoclay hemostatic nanocomposite fiber made by the methods according to the embodiments discussed above is provided, wherein the nanoclay is halloysite.

According to yet another embodiment of the present technology, an anti-hemorrhagic agent is provided. The anti-hemorrhagic agent includes a matrix of cellulose nanofibers, and a plurality of halloysite nanoclay particles attached to the matrix of cellulose nanofibers. The anti-hemorrhagic agent is configured to coagulate human plasma in an average time of about 143 seconds.

In some embodiments, the plurality of halloysite nanoclay particles are attached to the matrix of cellulose nanofibers via a wet-wet electrospinning process. In some embodiments, the wet-wet electrospinning process includes the steps of preparing a homogenous cellulose solution including cellulose and a room temperature ionic liquid, preparing a nanoclay suspension including halloysite and distilled water, electrospinning the cellulose solution into a first bath including the nanoclay suspension, transferring solidified cellulose—halloysite fibers from the first bath to a second bath including ethanol and distilled water, removing the solidified cellulose—halloysite fibers from the second bath, and freeze-drying the solidified cellulose—halloysite fibers.

In some embodiments, the anti-hemorrhagic agent further includes an article for applying the anti-hemorrhagic agent to a hemorrhage of a human user.

According to an alternative embodiment of the present technology, a system of coagulating human plasma is provided. The system includes an article having a cellulose—halloysite hemostatic nanocomposite fiber, and a human user having a hemorrhage. The article is configured to apply the cellulose—halloysite hemostatic nanocomposite fiber to the hemorrhage.

In some embodiments, the cellulose—halloysite hemostatic nanocomposite fiber is made by a wet-wet electrospinning process. In some embodiments, the wet-wet electrospinning process includes the steps of preparing a homogenous cellulose solution including cellulose and a room temperature ionic liquid, preparing a nanoclay suspension including halloysite and distilled water, electrospinning the cellulose solution into a first bath including the nanoclay suspension, transferring solidified cellulose—halloysite fibers from the first bath to a second bath including ethanol and distilled water, removing the solidified cellulose—halloysite fibers from the second bath, and freeze-drying the solidified cellulose—halloysite fibers.

In some embodiments, the cellulose—halloysite hemostatic nanocomposite fiber is configured to coagulate human plasma in an average time of about 143 seconds.

DETAILED DESCRIPTION

As used herein when describing a measuring numerical value, the term "about" includes the specific numerical value and a reasonable range encompassing the specific numerical value to account for, e.g., errors inherent in the measuring equipment used and in the humans handling such equipment. The reasonable range can be ±5%, or even ±10% of the specific numerical value. Thus, for example, a recitation of "about 100 nm" could reasonably include the range of 90-110 nm without departing from the spirit and scope of the present technology.

Figure 1:
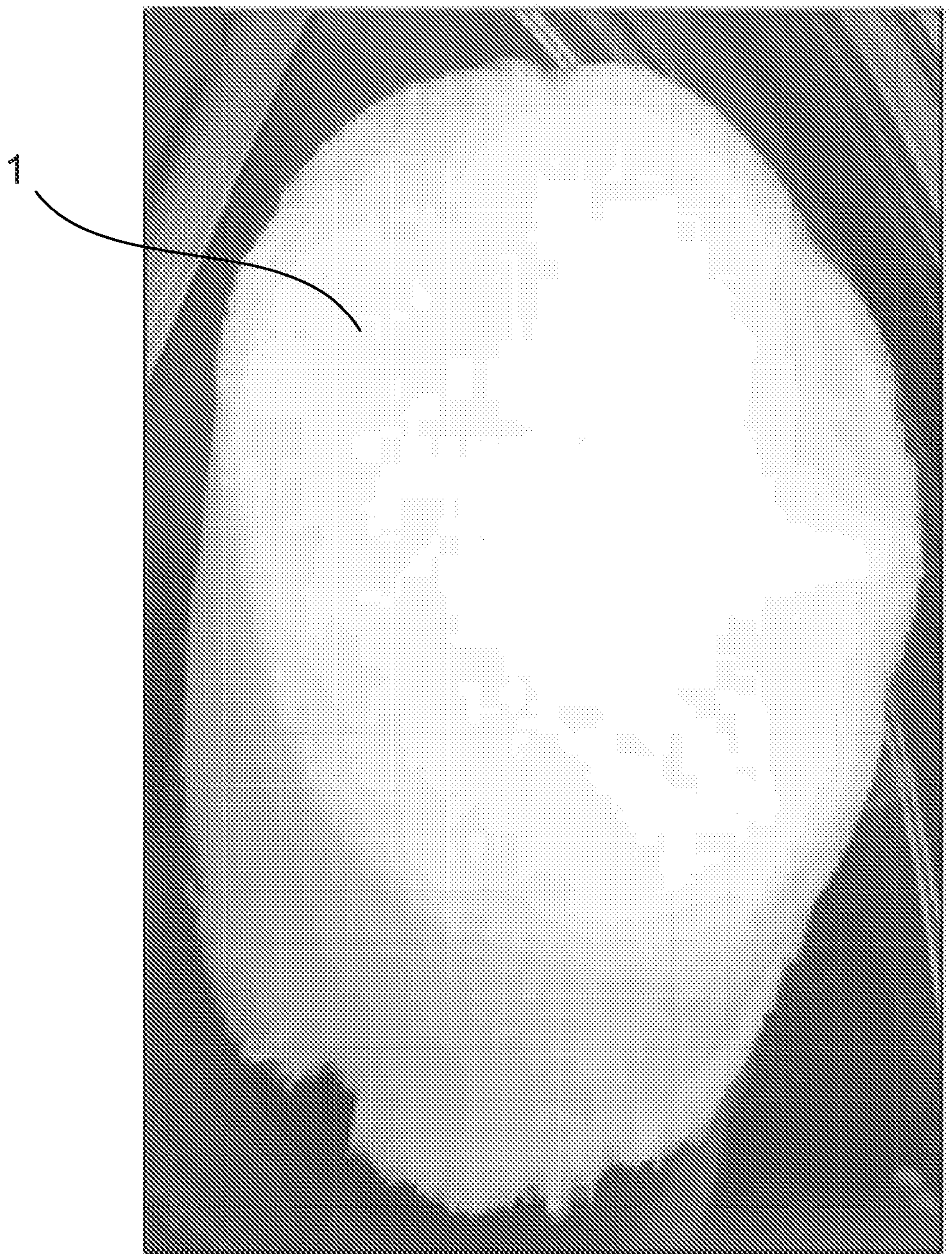
FIG. 1 is an isometric view of halloysite coated cellulose nanocomposite fibers according to an embodiment of the present technology.
Figure 2:
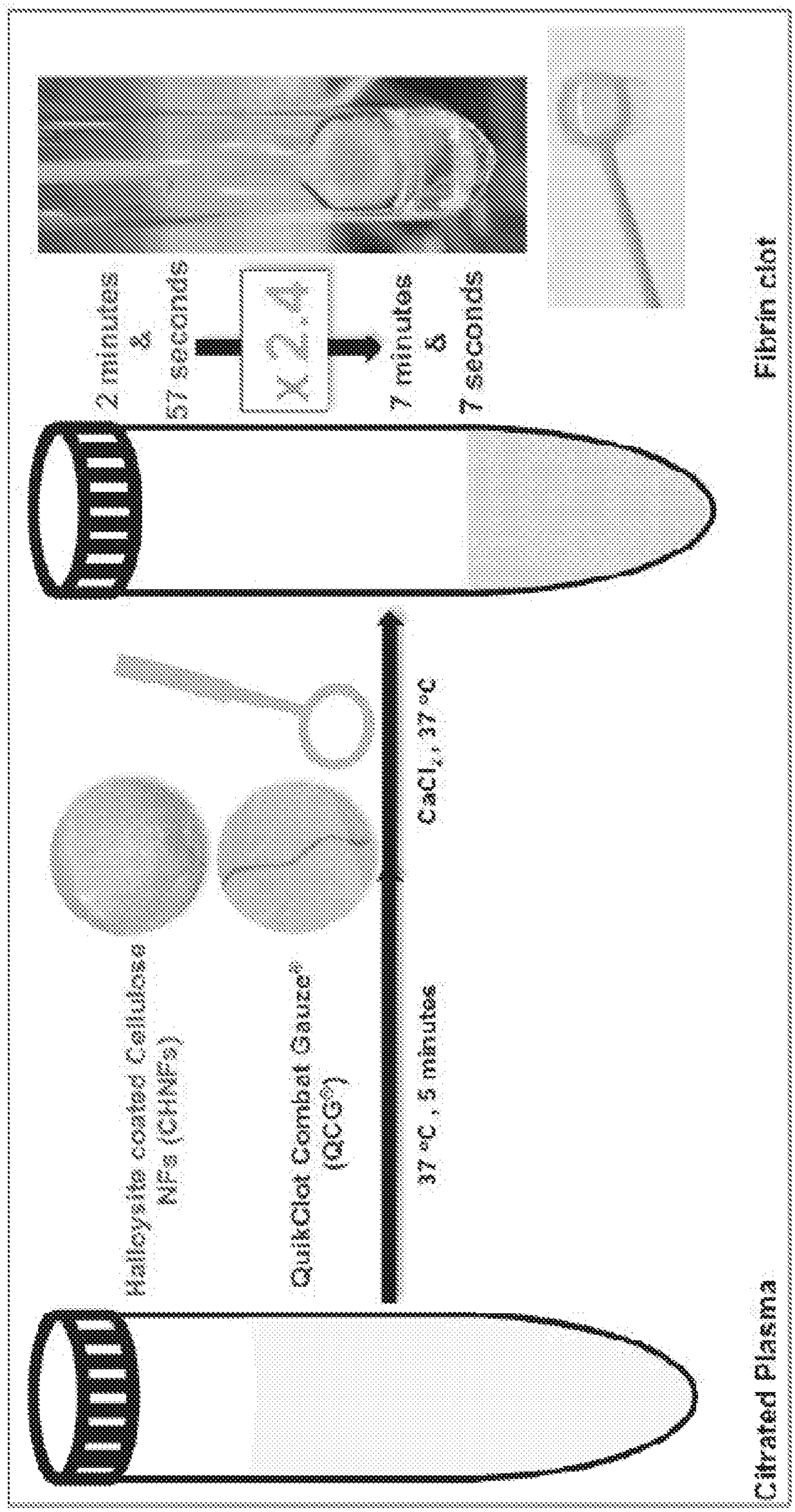
FIG. 2 is a flow chart comparing the plasma coagulation times of the halloysite coated cellulose nanocomposite fibers of FIG. 1 to QCG.

Referring now to FIGS. 1-2, some embodiments of the systems and methods of the present technology are directed to cellulose—nanoclay hemostatic nanocomposite fibers ("CHNF"). In some embodiments, the nanoclay is formed of an aluminosilicate clay. In preferred embodiments, the nanoclay is halloysite clay. In some embodiments, the fibers include nanocomposite fibers coated with halloysite, CHNFs 1, such as that shown in FIG. 1 after collection and freeze-drying. In some embodiments, the CHNFs 1 have an average diameter in the range of about 190 nm to about 710 nm. In some embodiments, the CHNFs 1 have an average diameter of about 450 nm. In some embodiments, the CHNFs 1 show 7-fold greater clay loading than QCG, and the CHNFs' 1 small average diameter of 450±260 nm affords a greater specific surface area (about 33.6 $m^2\ g^{-1}$) than the larger average diameter of 12.6±0.9 μm for QCG, which has a specific surface area of 1.6 $m^2\ g^{-1}$.

Figure 3A:
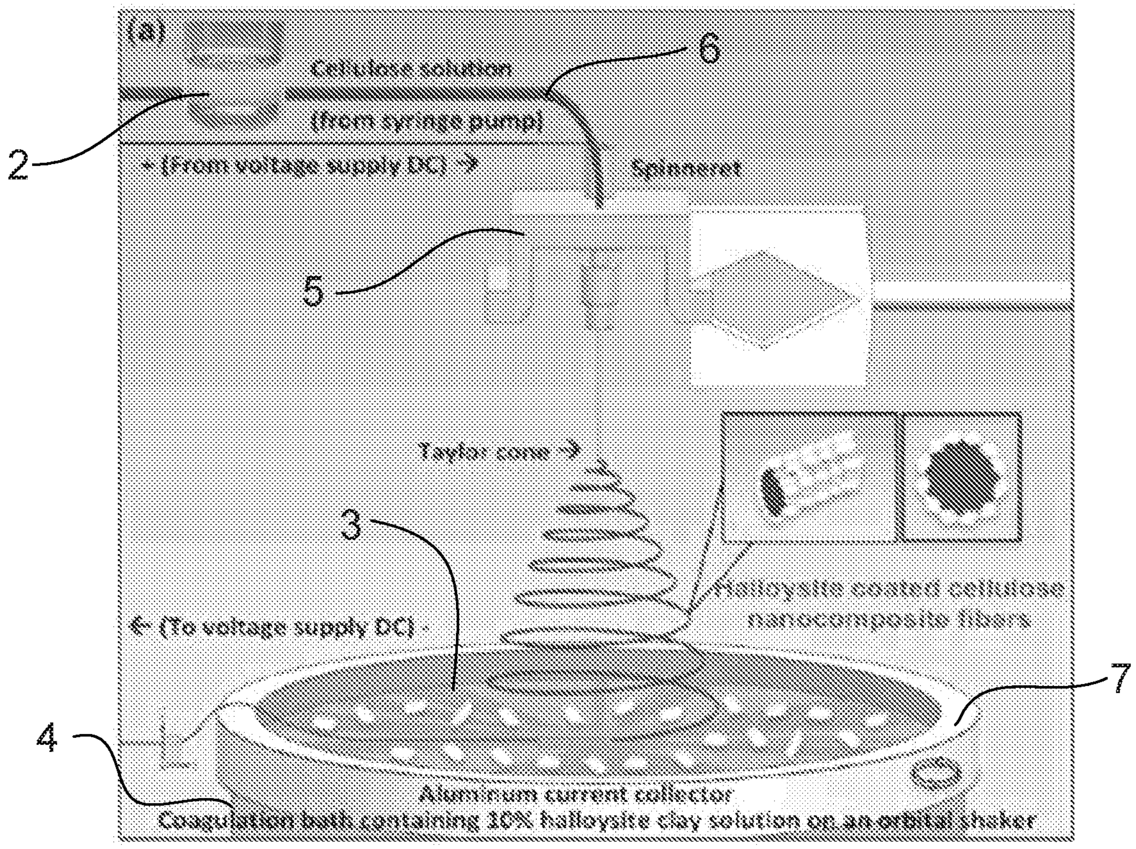
FIG. 3A is a schematic chart of a wet-wet electrospinning process according to an embodiment of the present technology.
Figure 3B:
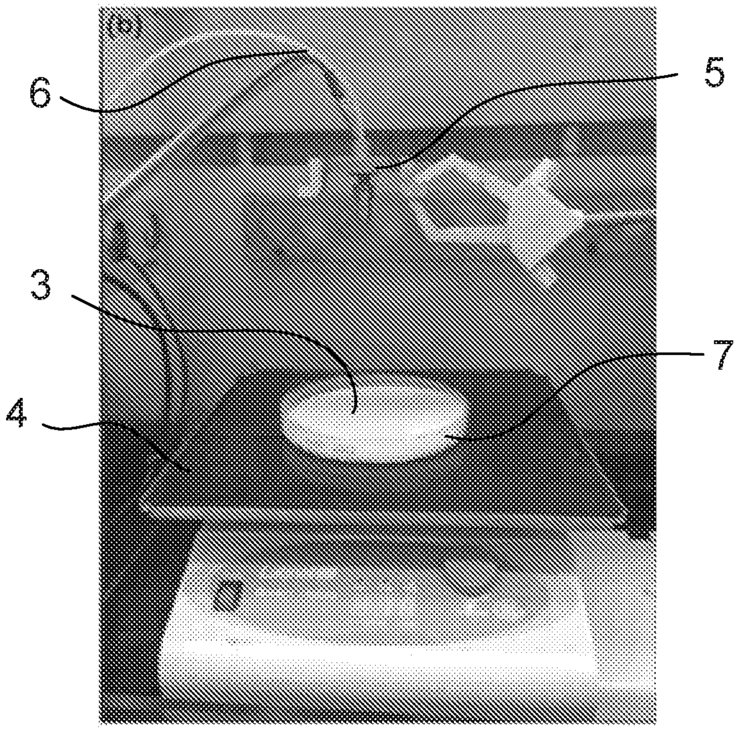
FIG. 3B is an isometric view of the wet-wet electrospinning process of FIG. 3A.

Referring now to FIGS. 3A-3B, in some embodiments, the CHNFs 1 are fabricated using a one-step wet-wet electrospinning process, where FIG. 3A is an exemplary schematic of the process and FIG. 3B is an isometric view of an exemplary wet-wet electrospinning process. Halloysite ($Al_2Si_2O_5(OH)_4.2H_2O$) is a naturally-occurring aluminosilicate nanoclay that exhibits a unique hollow tubular scroll structure. Halloysite is biocompatible and promotes blood coagulation. In some embodiments, cellulose is the matrix on which to immobilize the nanoclay due to its biocompatibility and low cost. Electrospinning can be used for preparing synthetic micro- and nano-polymeric fibers from solutions of polymers in volatile organic solvents. However, the biopolymer cellulose is a complex polysaccharide that does not dissolve in volatile organic solvents due to its extensive hydrogen-bonding network. Thus, in some embodiments, a non-volatile solvent is used for electrospinning cellulose. In preferred embodiments, a special class of non-volatile solvents, known as room temperature ionic liquids ("RTIL"), is used for electrospinning cellulose. The electrospinning of cellulose from a non-volatile RTIL, referred to as wet-wet electrospinning, is quite different from the conventional wet-dry electrospinning of a synthetic polymer from a volatile organic solvent. In wet-wet electrospinning, a biopolymer, such as cellulose, is dissolved in a non-volatile primary solvent, preferably an RTIL, which is miscible with a secondary solvent, such as water, alcohol (e.g., ethanol), or combinations thereof, in a coagulation bath collector. In some embodiments, this secondary solvent selected for use in the coagulation bath is a non-solvent of the polymer to promote its precipitation in the coagulation bath.

In some embodiments, the wet-wet electrospinning technique was employed to produce cellulose nanofibers ("CNF") and CHNFs 1 n a one-step process. In conventional wet-dry electrospinning, synthetic polymers are dissolved in volatile organic solvents, which rapidly evaporate upon the exit of the fiber jet from the needle forming a fiber mat on dry metal collectors. In contrast, in wet-wet electrospinning, a polymer is dissolved in a non-volatile primary solvent and electrospun into a coagulation bath collector containing a secondary non-solvent for the polymer. Primary solvent, in which the polymer is dissolved, is miscible with the secondary solvent so that the primary solvent is drawn away from the polymer resulting in its precipitation in the coagulation bath collector. Thus, in wet-wet electrospinning fiber formation occurs through precipitation in the coagulation bath, rather than through the solvent evaporation occurring in wet-dry electrospinning.

In some embodiments, cellulose was dissolved in RTIL and electrospun into a water bath. As cellulose coagulates it forms an intermediate hydrogel with water migrating into the fibers concomitant with RTIL diffusion into the water bath. The hydrogel ultimately collapses into CNFs that are collected and, in some embodiments, freeze-dried to obtain nonwoven cellulose nanofiber balls. In contrast, simple air-drying causes, in some embodiments, a collapse of morphology resulting in a cellulose mat. In some embodiments, the coagulation bath containing water is replaced with an aqueous suspension of halloysite nanoclay, resulting in the intermediate hydrogel entraining halloysite in the surface of the CNFs, and cellulose—halloysite nanofiber balls are collected by freeze-drying. This process physically embeds halloysite clay nanoparticles primarily on the surface of the fibers during the intermediate hydrogel state of cellulose in the coagulation bath. The freeze-dried CHNFs 1 appear identical to cotton balls but with an off-white color due to their halloysite surface, as shown in FIG. 1.

In some embodiments, cotton balls (1.06 g) were mixed with 50.0 g of RTIL ([EMTM][Ac] density=1.027 g/mL) using a magnetic stirrer at 80° C. for 12 h to obtain a 2.12% (w/w) homogenous cellulose solution 2. A halloysite nanoclay suspension 3 (10% (w/v)) was prepared by mixing 10 g of halloysite nanoclay in 100 mL of distilled water. The clay solution was then transferred to a large glass petri dish and placed on top of an orbital shaker 4. A small piece of aluminum foil was placed inside the petri dish and connected to the negative lead of a high voltage supply using electrically insulated copper wires. In some embodiments, the high voltage electrospinning system is capable of generating a DC voltage up to 30 kV. The electrospinning parameters, i.e., needle diameter, distance between electrodes, polymer concentration, flow rate, etc., were optimized by an interactive approach.

As shown in FIG. 3A, in some embodiments, the cellulose solution 2 was placed in a syringe (10 mL) that connected to a spinneret 5 with a fitted aluminum needle. The needle used has a blunt tip with an internal diameter of 0.635 mm (23 Gauge). Polytetrafluoroethylene tubing 6 delivered the cellulose solution 2 from the syringe to the spinneret 5. The spinneret 5 was connected to the positive terminal of the high voltage supply. The distance between the tip of the aluminum needle and the surface of the clay solution 3 was fixed at 10 cm. Finally, a high voltage of 18 kV was applied between the spinneret 5 set-up and the coagulation bath 7 as the cellulose solution 2 was pumped at a constant rate of 60 pL/min into the clay suspension 3 (in coagulation bath 7) using, in some embodiments, a mechanical syringe pump. The orbital shaker 4 was run at 70 rpm to prevent sedimentation of clay on the bottom of the petri dish. In some embodiments, after the spinning process, the solidified cellulose-halloysite fibers were removed from the coagulation bath 7 and transferred into a clean 50% distilled water-ethanol bath to further remove ionic liquid from the fibers. In some embodiments, the fibers were freeze-dried to obtain the halloysite clay coated cellulose nanofibers, or CHNFs 1, as shown in FIG. 1.

In some embodiments, this electrospinning process was repeated using a distilled water coagulation bath instead of the halloysite nanoclay suspension to produce CNFs as a negative control. CNFs after electrospinning were mixed with halloysite clay ("MCNF") and used as a second control to evaluate the commonly used method of fiber production in the commercial products discussed above. This process for producing MCNFs involves immersing electrospun cellulose nanofibers in a halloysite nanoclay suspension (10% (w/v)) for 24 h. The MCNFs were then transferred into a clean 50% distilled water-ethanol bath for a washing step. Finally, the fibers were freeze-dried to obtain the halloysite clay mixed cellulose nanofibers, MCNFs. All of the electrospinning processes were carried out inside an anti-static polycarbonate box within a standard laboratory fume hood at 20±3° C. with a relative humidity controlled at 59±5%. In some embodiments, a digital humidity and temperature monitor was used to measure the temperature and the relative humidity.

Figure 4:
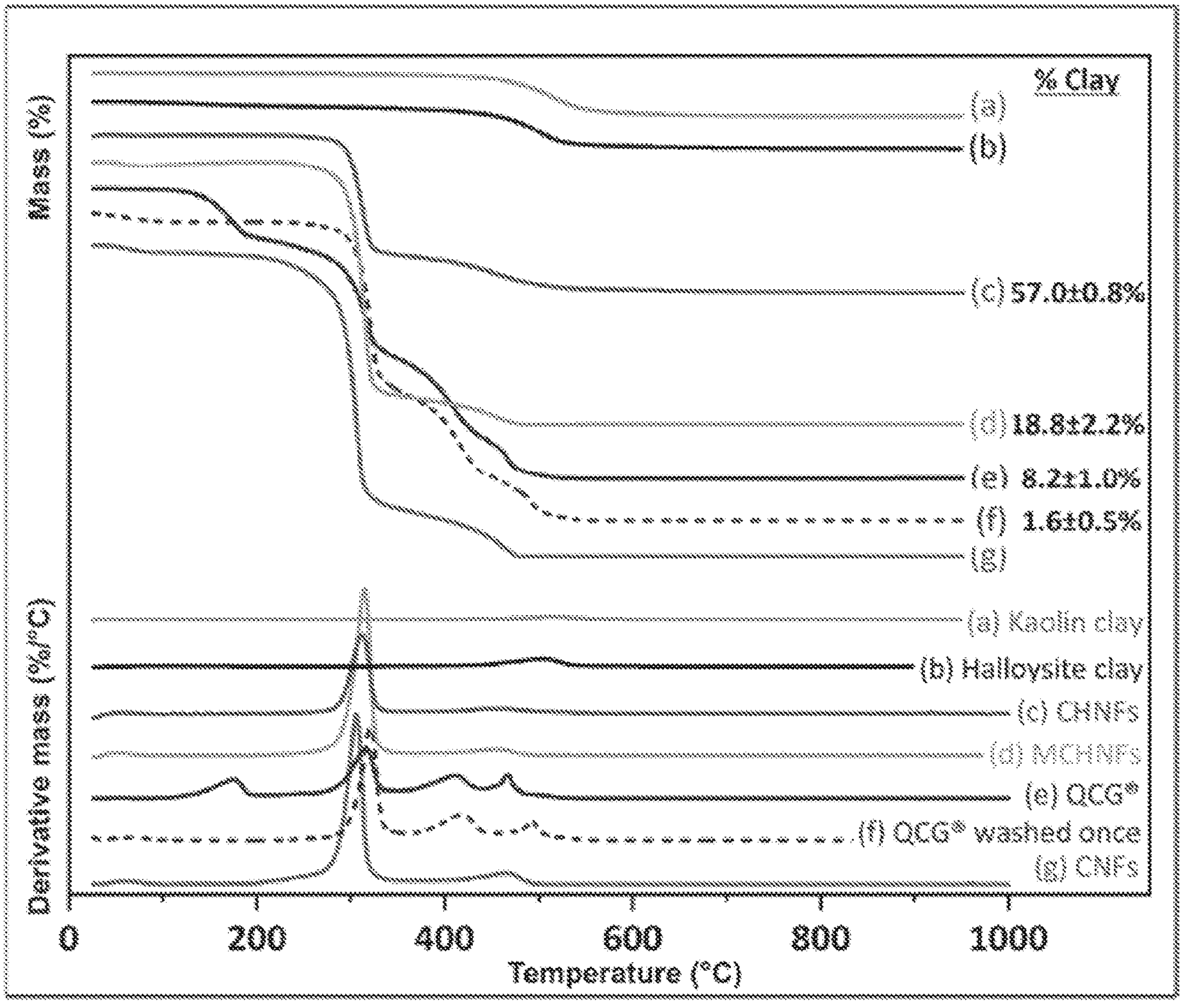
FIG. 4 is a chart showing a thermogravimetric analysis comparing the amounts of clay in various fiber composites.

Referring now to FIG. 4, in some embodiments, thermogravimetric analysis shows that the CHNFs 1 left the higher residual mass at 1000° C. when compared to MCNFs and QCG (n=3, P<0.05). The residual mass corresponds to halloysite nanoclay and the amount of clay present in the CHNFs was calculated to be 57.0±0.8%. In contrast, the MCNFs contained only 18.8±2.2% halloysite nanoclay. Thus, the fabrication process according to the present technology is superior to the present commercial processes. Similarly, the amount of kaolin clay in QCG based on residual mass was 8.2±1.0%, and this amount was reduced to 1.6±0.5% after a single washing step. Thus, in some embodiments, CHNFs 1 have approximately 7-times more active clay than QCG.

The major mass loss of neat halloysite and kaolin clay occurred over the temperature range of 400-600° C., consistent with the dehydroxylation of structural Al-OH groups in the endothermic dehydration of clay. The CHNFs 1 showed the two characteristic decompositions associated with combustion and smoldering of cellulose taking place at 200-350° C. and 400-500° C., respectively. The purity of CHNFs 1 was substantiated by the absence of decomposition peaks associated hemicellulose (~220° C.) and lignin (~100° C.) impurities.

Figure 5A:
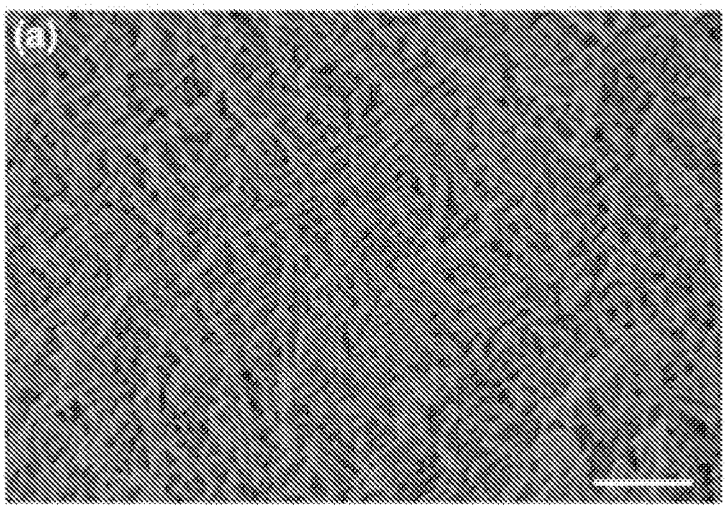
FIG. 5A is an SEM image of halloysite nanoclay at 50,000 magnification.
Figure 5B:
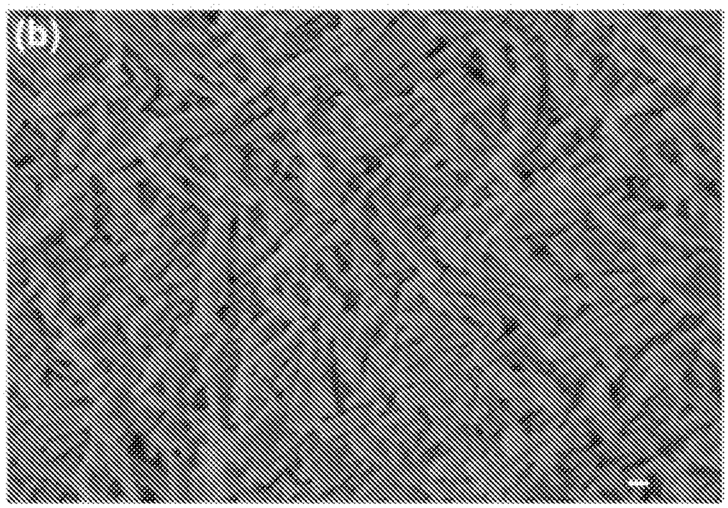
FIG. 5B is an SEM image of halloysite nanoclay at 100,000 magnification.
Figure 5C:
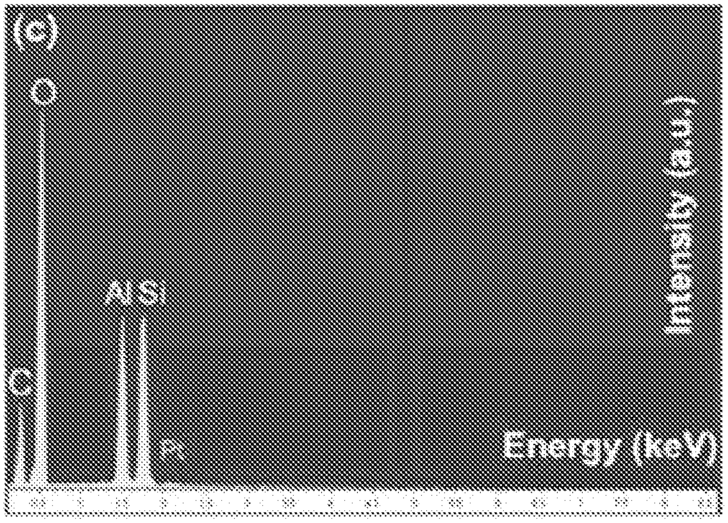
FIG. 5C is an EDX spectrum of halloysite nanoclay.
Figure 5D:
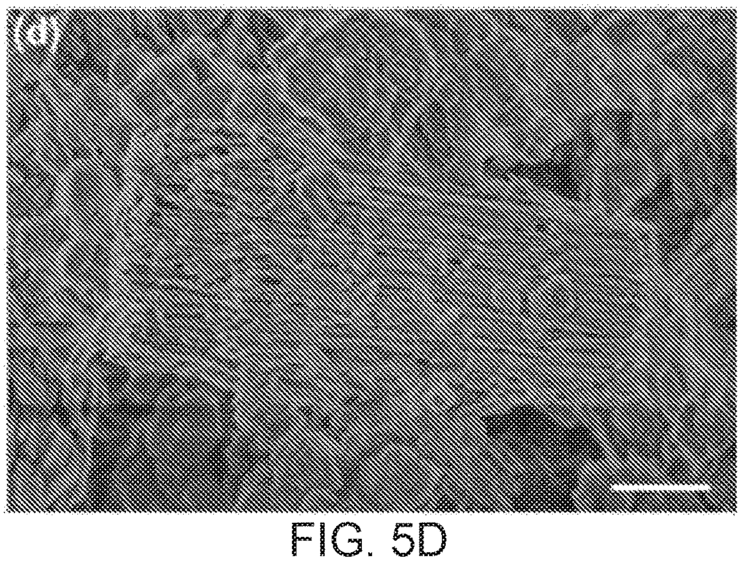
FIG. 5D is an SEM image of kaolin clay at 50,000 magnification.
Figure 5E:
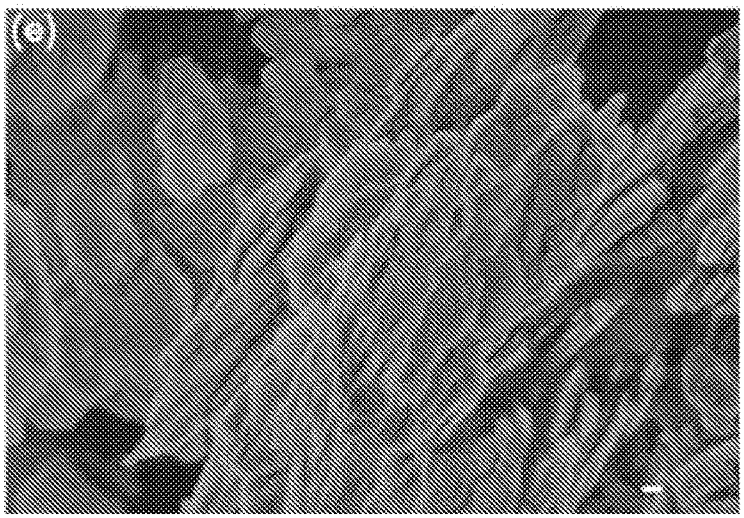
FIG. 5E is an SEM image of kaolin clay at 100,000 magnification.
Figure 5F:
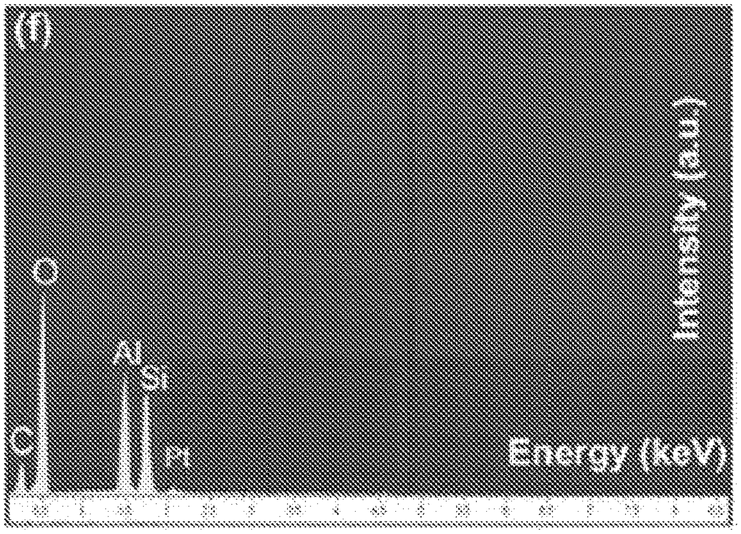
FIG. 5F is an EDX spectrum of kaolin clay.

Referring now to FIGS. 5A-5F, in some embodiments, morphology and the elemental composition of the clay samples were studied via SEM. FIGS. 5A and 5B show SEM images of halloysite nanoclay at magnifications of 50,000 and 100,000, respectively. FIGS. 5D and 5E show SEM images of kaolin clay at magnifications of 50,000 and 100,000, respectively. FIGS. 5C and 5F show EDX spectra of halloysite nanoclay and kaolin clay, respectively. The scale bars are 1 μm (FIGS. 5A and 5D) and 100 nm (FIGS. 5B and 5E). In some embodiments, the halloysite nanoclay appeared to have the typical tubular morphology with diameters ranging from 30-120 nm. The SEM images showed the common plate morphology of kaolin clay, the clotting agent used in QCG (FIGS. 5D and 5E). In contrast to halloysite nanoclay, kaolin clay flakes stack together to form large agglomerates (FIG. 5D). EDX analysis of both clay samples showed the same elemental composition as they are chemically identical (FIGS. 5C and 5F).

Figure 6A:
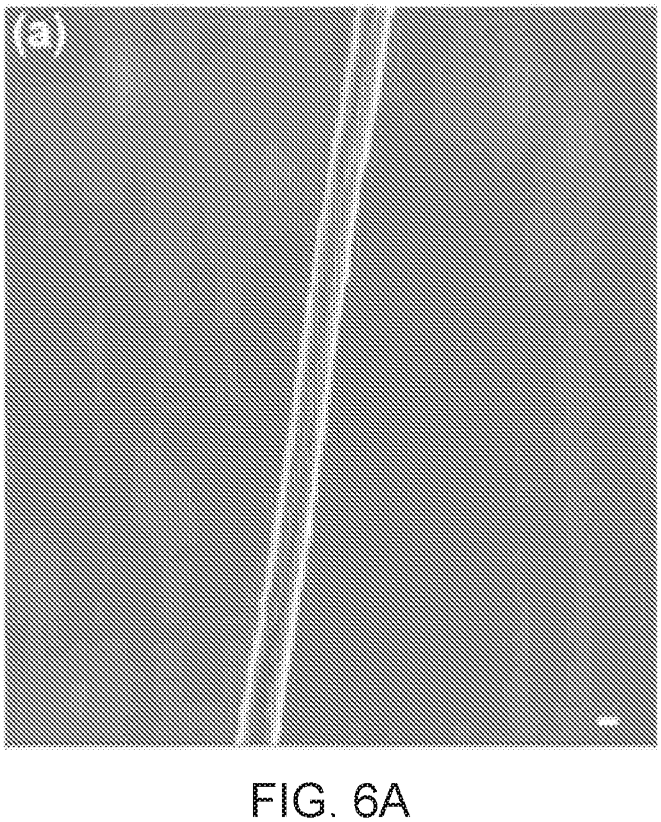
FIG. 6A is an SEM image of an electrospun CNF at 100,000 magnification.
Figure 6B:
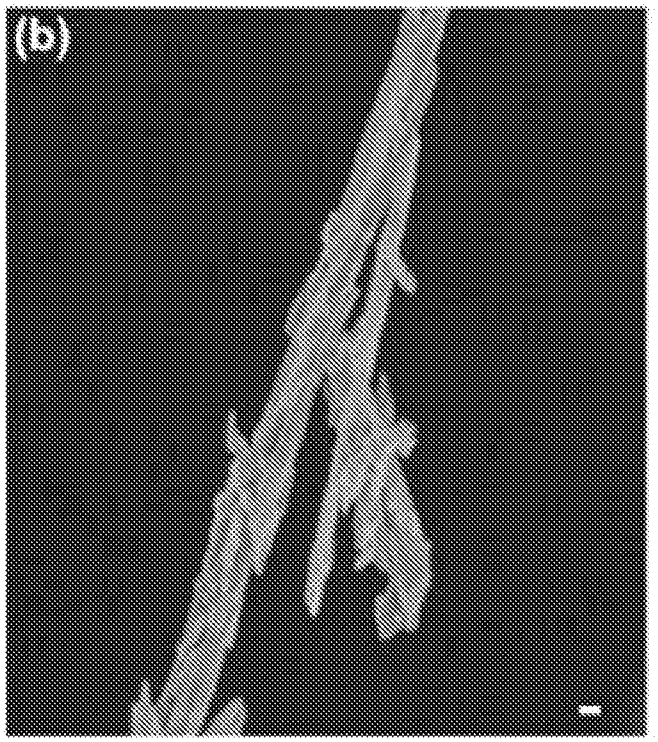
FIG. 6B is am SEM image of an electrospun CHNF washed once at 100,000 magnification.
Figure 6C:
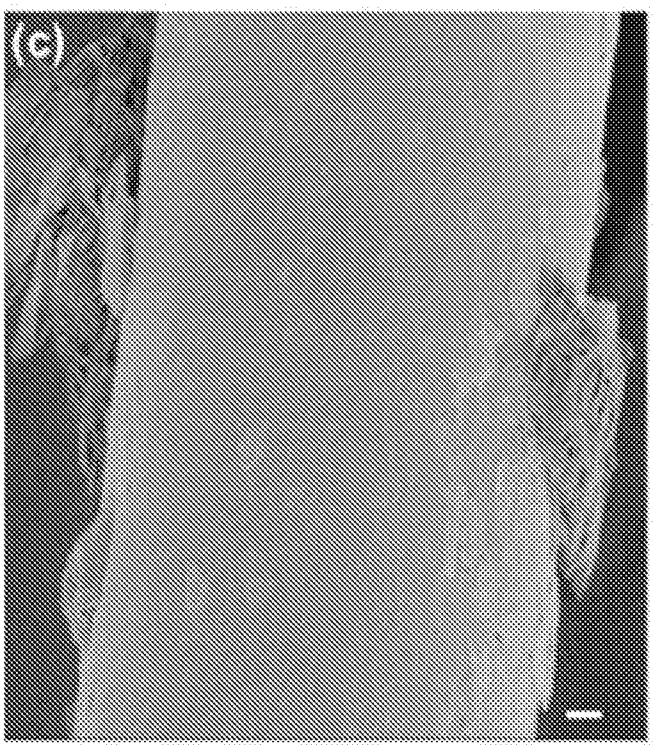
FIG. 6C is an SEM image of a microfiber of QCG at 20,000 magnification.
Figure 6D:
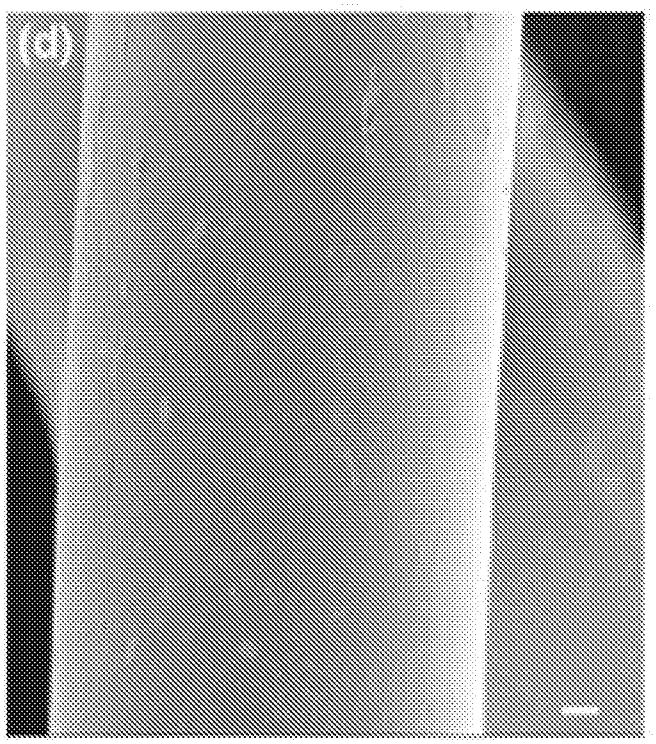
FIG. 6D is an SEM image of a microfiber of QCG washed once at 20,000 magnification.
Figure 6E:
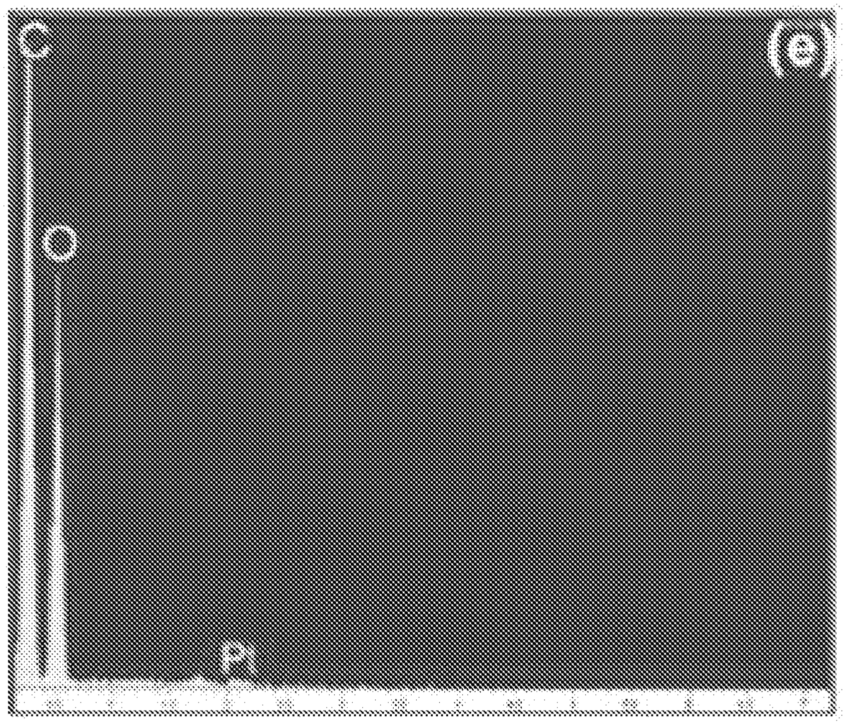
FIG. 6E is an EDX spectrum of an electrospun CNF.
Figure 6F:
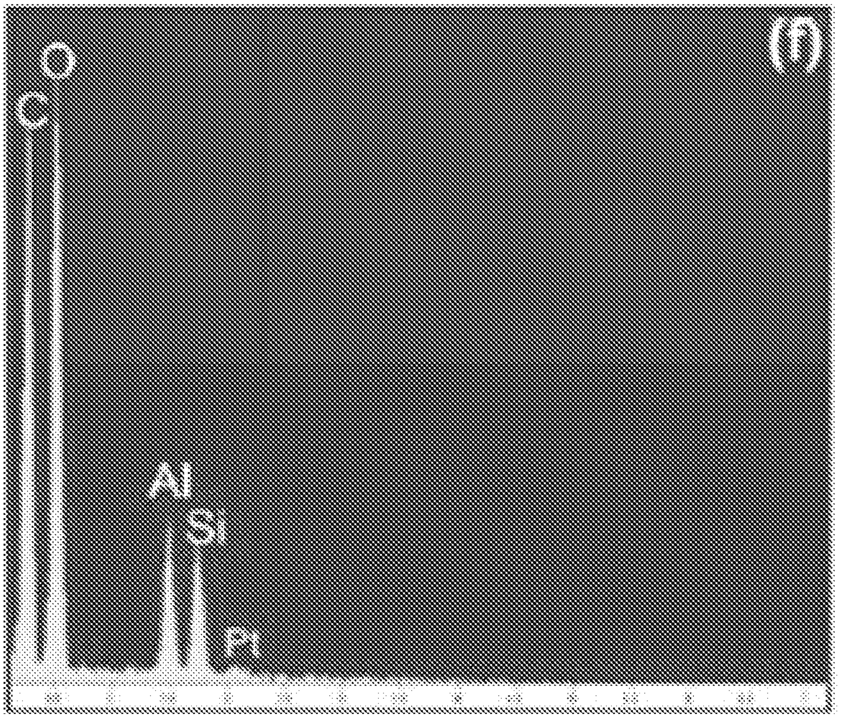
FIG. 6F is an EDX spectrum of an electrospun CHNF washed once.
Figure 6G:
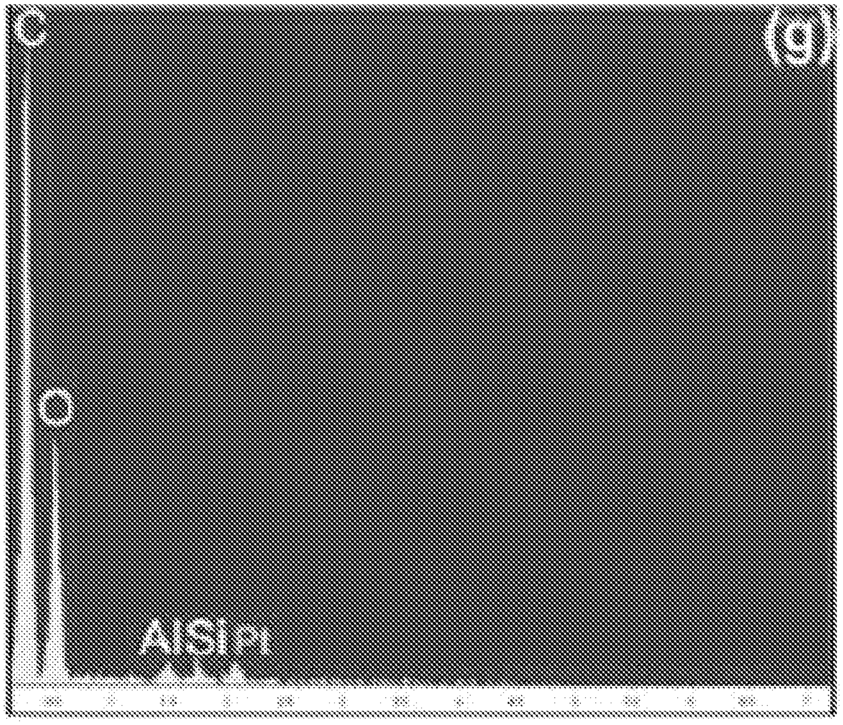
FIG. 6G is an EDX spectrum of a microfiber of QCG.
Figure 6H:
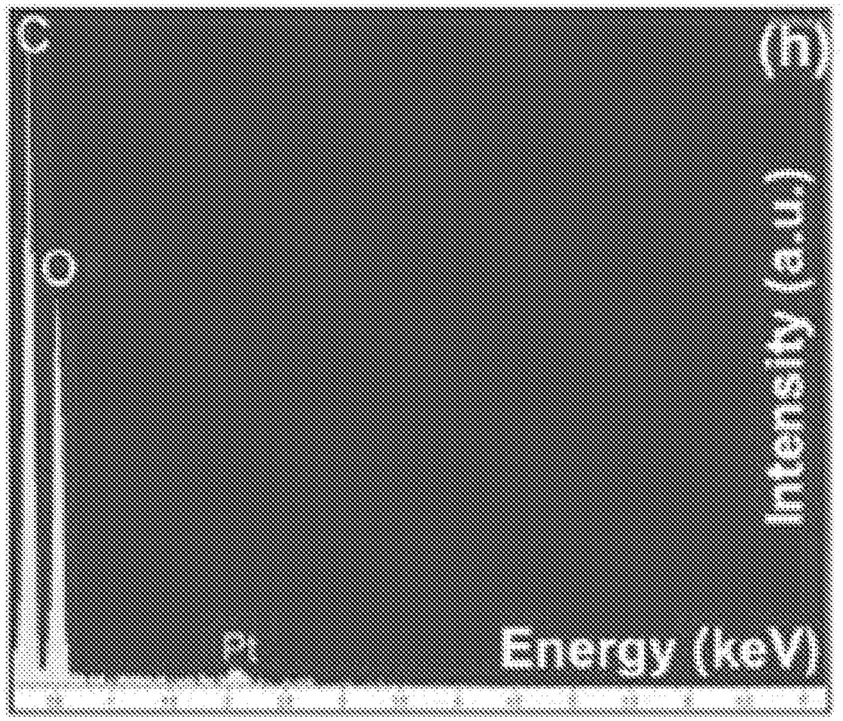
FIG. 6H is an EDX spectrum of a microfiber of QCG washed once.
Figures 7A, 7B, 7C:
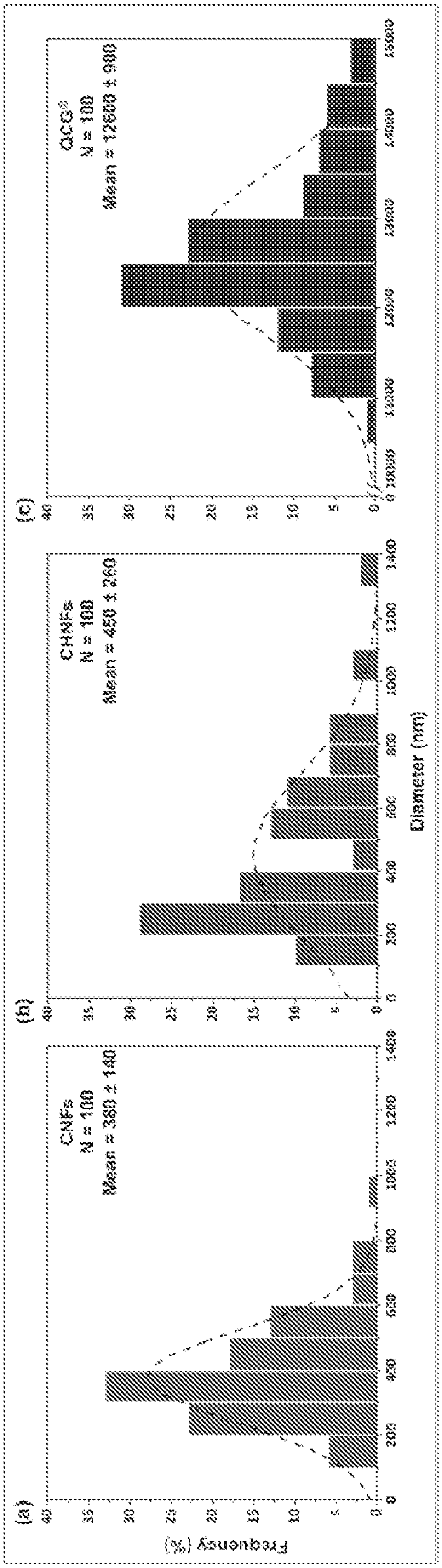
FIG. 7A is a histogram chart of the diameter distribution of a CNF.
FIG. 7B is a histogram chart of the diameter distribution of a CHNF.
FIG. 7C is a histogram chart of the diameter distribution of a QCG.

Referring now to FIGS. 6A-7C, in some embodiments, morphology and the elemental composition of the fiber samples were studied via SEM at image (FIG. 6A) and EDX spectrum (FIG. 6E) of an electrospun CHNF 1 at magnification of 100,000, SEM image (FIG. 6B) and EDX spectrum (FIG. 6F) of an electrospun CHNF 1 washed once at magnification of 100,000, SEM image (FIG. 6C) and EDX spectrum (FIG. 6G) of a microfiber of QCG at magnification of 20,000, and SEM image (FIG. 6D) & EDX spectrum (FIG. 6H) of a microfiber of QCG washed once at magnification of 20,000. The scale bars are 100 nm (FIGS. 6A and 6B) and 1 μm (FIGS. 6C and 6D). In some embodiments, electrospun cellulose nanofibers have a cylindrical structure (as shown in FIG. 6A) with an average diameter of 380±140 nm (as shown in FIG. 7A). FIGS. 7A-7C show histograms of the diameter distribution of the fiber samples. Fiber diameter histograms of cellulose (FIG. 7A), CHNFs 1 (FIG. 7B) QCG (FIG. 7C) observed during SEM imaging ($P<0.05$).

The EDX spectrum of cellulose (FIG. 6E) reveals the characteristic Kα1 x-ray peaks corresponding to carbon (0.277 keV) and oxygen (0.525 keV). CHNFs 1 were much smaller in size (FIG. 6B) with an average diameter of 450±260 nm (FIG. 7B). In contrast, QCG is composed of micron size fibers ranging from 11 to 15 μm with an average diameter of 12.6±0.9 μm (FIG. 7C).

In preferred embodiments, the surface of CHNFs 1 is completely covered with halloysite nanoclay particles. In contrast, QCG has a sparse kaolin clay coating of the microfiber, as shown in FIG. 6C. As shown in FIG. 6F, the EDX spectrum of CHNFs 1 shows, in some embodiments, higher intensity Kα1 x-ray peaks, for A1 (1.487 keV) and Si (1.740 keV), than those observed in the EDX spectrum of QCG (FIG. 6G). The loss of significant amounts of kaolin clay after a single water wash was evident in the SEM image of washed QCG (FIG. 6D). This observation was confirmed by the absence of the characteristic A1 and Si x-ray peaks in the EDX spectrum of washed QCG (FIG. 6H).

In some embodiments, XRD analysis further supported the determinations made based on the TGA, SEM, and EDX studies discussed above. In some embodiments, the XRD pattern of CHNFs 1 was identical to the neat halloysite nanoclay, and peaks belonging to cellulose were not apparent. This verifies the abundance of halloysite nanoclay coating on the surface of the CHNFs 1. In contrast, the XRD pattern of QCG showed broad peaks belonging to cellulose along with the two most intense peaks originating from the kaolin clay. These two peaks were not observed in the XRD pattern of the washed QCG. This supports the conclusion that most of the kaolin clay on the fiber was lost after a single washing step. Moreover, the crystallinity of both halloysite and kaolin clay was retained in the composite fibers.

Figures 8A, 8B, 8C, 8D:
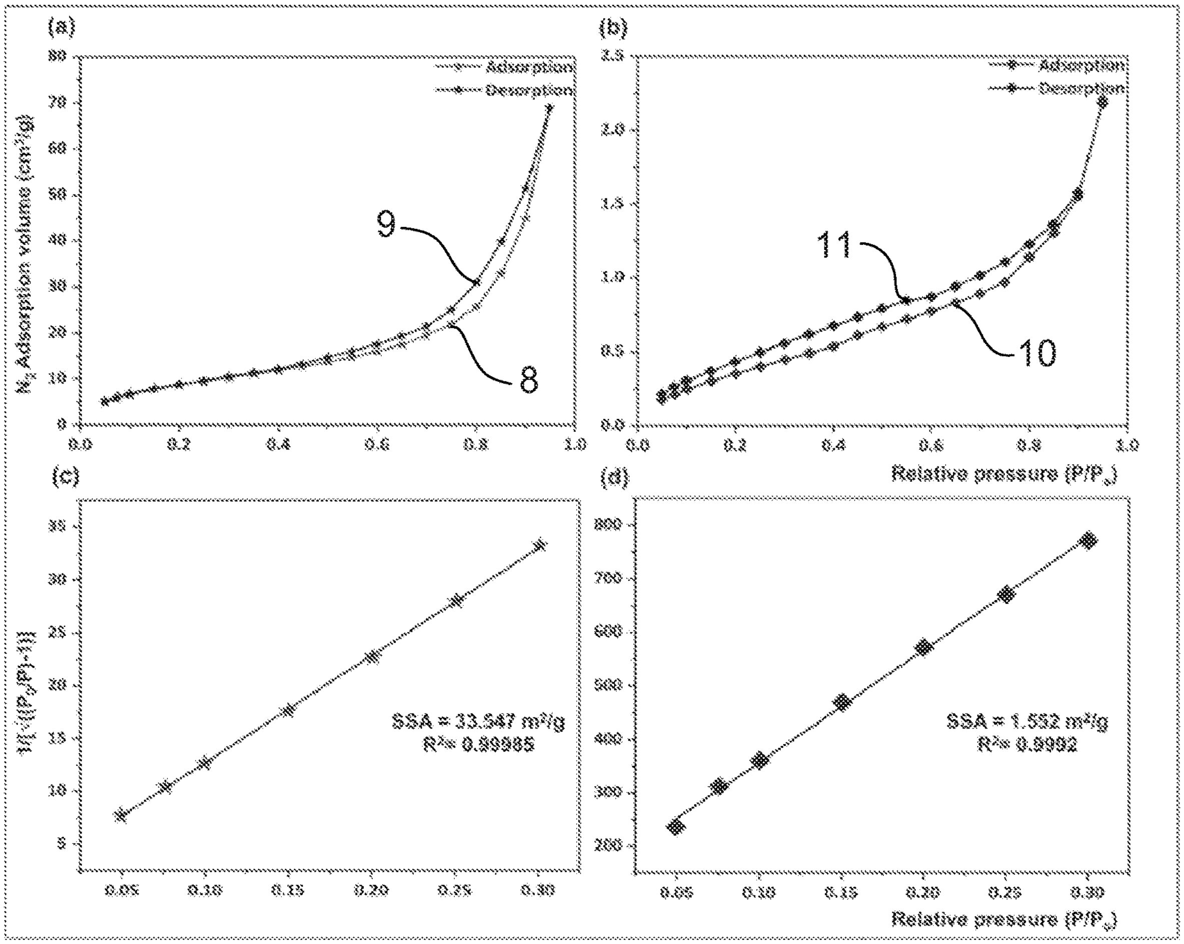
FIG. 8A is a surface area analysis chart showing nitrogen adsorption—desorption isotherms of CHNF.
FIG. 8B is a surface area analysis chart showing nitrogen adsorption—desorption isotherms of QCG.
FIG. 8C is a surface area analysis chart showing BET plots/Langmuir fits of CHNF.
FIG. 8D is a surface area analysis chart showing BET plots/Langmuir fits of QCG.

Referring now to FIGS. 8A-8D, in some embodiments, the specific surface area of the composite fibers was calculated using nitrogen adsorption-desorption isotherms (FIGS. 8A-8B) and the BET plots/Langmuir fits (FIGS. 8C-8D) of CHNFs 1 (FIGS. 8A and 8C) and QCG (FIGS. 8B and 8D). FIG. 8A shows adsorption plotting 8 and desorption plotting 9 of CHNFs 1. FIG. 8B shows adsorption plotting 10 and desorption plotting 11 of QCG. CHNFs 1 showed significantly higher specific surface area (33.6 $m^2 g^{-1}$) than QCG (1.6 $m^2 g^{-1}$). This represents nearly 6-times the specific surface area of CNFs (5.7 $m^2 g^{-1}$). In some embodiments, the additional surface area of CHNFs 1 results from the nanoclay particles coating on the fiber surface. The specific surface area of the washed QCG was 3.5 $m^2 g^{-1}$. This corresponds to approximately 125% increase in specific surface area of QCG. This likely results from the removal of large flaky agglomerates of kaolin clay from the QCG fibers during the washing step.

The TGA, SEM, EDX, XRD, and BET characterization results all conclusively demonstrate the removal of kaolin clay from QCG even after a single washing step. Thus, in severe bleeding cases, or similar wetting in the field, the procoagulant clay particles are rapidly lost, reducing the procoagulant activity of QCG. In contrast, the CHNFs 1 show, in preferred embodiments, both a higher initial clay loading and remarkably less leaching of halloysite nanoclay particles from the fibers.

Figure 9:
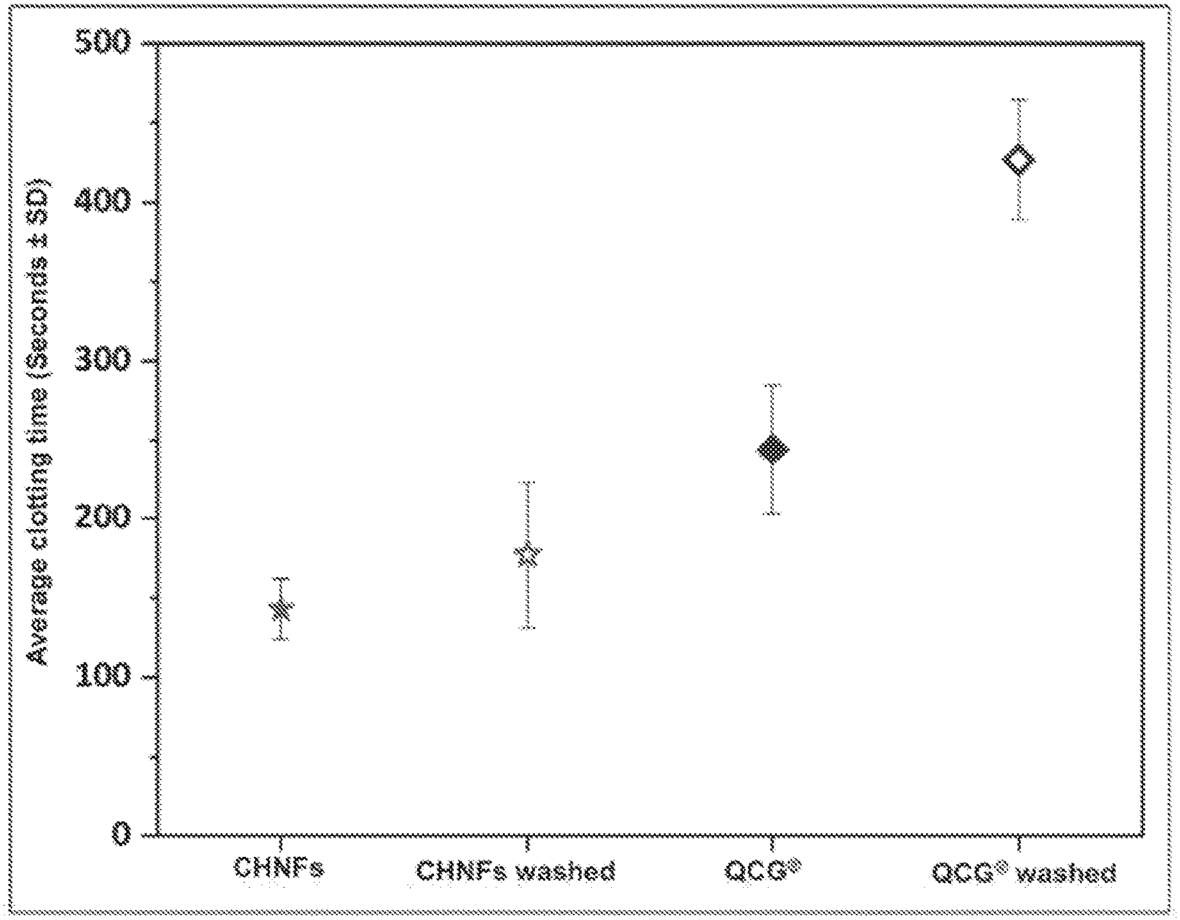
FIG. 9 is an aPTT assay chart showing the time taken to form a fibrin clot in a citrated plasma sample for CHNF, CHNF washed once, QCG, and QCG washed once.

In some embodiments, the procoagulant activity and stability of the CHNFs 1 were confirmed by plasma clotting studies using activated Partial Thromboplastin Time ("aPTT") assay, which shows the time taken to form a fibrin clot in a citrated plasma sample. As shown in FIG. 9, the CHNFs 1 generate the fastest average plasma coagulation time (143 ±19 seconds) of all samples tested. In some embodiments, the CHNFs 1 generate an average plasma coagulation time in the range of about 124 seconds to about 162 seconds. In some embodiments, the CHNFs 1 generate an average plasma coagulation time of about 143 seconds. This coagulation time is 2.4-times faster than that observed for QCG, which is 244 ±41 seconds. Both CHNFs 1 and QCG performed better than CNFs, which took over 27 min to coagulate plasma. CHNFs 1 and QCG both showed reduced pro-coagulant performance after a single washing with water, although CHNFs 1 clotting performance reduced by only 24% compared to a 75% performance loss for QCG, as shown in FIG. 9. Additionally, the CHNF 1 composite in this embodiment had also been thoroughly washed with both water and ethanol in its preparation to remove residual ionic liquid. Thus, it is not surprising that additional washing step of the CHNFs 1 with water resulted in only a slight reduction in procoagulant activity. An additional advantage of CHNFs 1 is that the average plasma coagulation time of halloysite clay is 55 seconds faster than kaolin clay, thus making halloysite nanoclay superior to kaolin.

EXAMPLES

In some embodiments, the CHNFs 1 formed by the wet-wet electrospinning process discussed above are thoroughly washed with alcohol-water mixture to remove residual RTIL. QCG, marketed by Z-MEDICA, EEC, approved by the United States Food and Drug Administration and also endorsed by the US Department of Defense for external use due to its ability of controlling severe arterial hemorrhage, was selected as the commercial standard to compare the procoagulant efficacy of these CHNFs 1.

In some embodiments, pure absorbent cotton balls, HPLC grade room temperature ionic liquid (RTIL), 1-ethyl-3-methylimidazolium acetate ([EMIM][Ac], >95.0%), absolute ethanol (>99.8%), and halloysite nanoclay were used. In some embodiments, kaolin clay and QCG were used. In some embodiments, citrated human plasma and an aPTT clinical diagnostic kit were used. In some embodiments, double-distilled water from an in-house water purification system was used.

In some embodiments, CHNFs 1, MCNFs, CNFs, and QCG were subjected to thermogravimetric analysis to deduce the amount of clay present in the fiber composites. The composite fibers before and after a water wash were also analyzed along with halloysite and kaolin clay controls. All the samples were heated from room temperature (25° C.) to 1000° C. at a constant heating rate of 10° C./min under dry atmospheric conditions.

In some embodiments, a field emission scanning electron microscope with energy dispersive X-ray spectroscopy was used to investigate the morphology and the elemental composition of the CHNFs 1. QCG was imaged before and after subjecting to a washing step to empirically evaluate the leaching of kaolin clay from the fibers. CNFs, halloysite nanoclay, and kaolin clay were also subjected to SEM and EDX analysis as controls. The average fiber diameters were calculated from 100 individual fibers from 10 identical electrospinning experiments were employed in this fiber diameter analysis.

In some embodiments, crystallinity of the clay in the CHNFs 1 and QCG were studied using an X-ray diffractometer, and were compared to the halloysite and kaolin clay controls. The crystallinity of the CNFs was also evaluated.

In some embodiments, the surface area of the CHNFs 1 was estimated by conducting a BET surface area analysis. A sample of CHNFs (117 mg) was degassed at 100° C. for 24 h. This was followed by N2 adsorption-desorption at 77.35 K (−196° C.) under a relative vapor pressure (P/P0) of 0.05-0.3. An electrospun CNF sample (70 mg) was used as a control in this experiment. QCG samples before (447 mg) and after (241 mg) undergoing a washing step was also subjected to surface area analysis using same experimental conditions as CHNFs.

In some embodiments, an aPTT assay was employed to evaluate human plasma coagulation performance of the CHNFs 1, QCG, clay controls, and CNFs using citrated human plasma. This assay is a two-step process that measures the time taken to form a fibrin clot in a citrated plasma sample. A sample of citrated human plasma (1 mL) was incubated with ~1 mg of fiber or clay sample (the activator) for 5 min followed by the addition of 500 μL of 25 mM calcium chloride solution at 37° C. A stopwatch was turned on immediately upon the introduction of the calcium chloride solution. An inoculating loop was used to detect the formation of the fibrin clot and the time taken to form the fibrin clot was recorded. This process was repeated with CHNFs 1 and QCG before and after subjecting to a washing step to evaluate the depletion of coagulation performance due to the loss of clay from the composite fibers. A positive control experiment was conducted using 200 μL of citrated human plasma, 100 μL of calcium chloride, and 100 μL of the particle-based Kontact activator (contains 1.2% rabbit brain phospholipid, 0.03% magnesium aluminum silica, 0.4% phenol, 0.8% buffer, salt, and stabilizers) of the aPTT assay. In some embodiments, the above clotting experiments were run in borosilicate glass culture tubes.

The composite fibers according to embodiments of the present technology will make a dramatic, lifesaving impact in the treatment of hemorrhages, such as those associated with traumatic injuries, surgical procedures, and frequent bleeding events. In some embodiments, the CHNFs 1 outperformed the present leading commercial product, QCG, as a topical blood clotting material by exhibiting 2.4-times faster plasma coagulation time. In some embodiments, the CHNFs 1 had three-times the clay anti-leaching performance compared with the QCG post-wetting. The drastic reduction of human plasma coagulation time renders the CHNFs 1 a potential life-saving material. The advantages of using the nanocomposites of the present technology over the commercially available products are that the materials used for fabrication are cheap, naturally occurring, and the CHNFs 1 retains its function for a longer period of time. In some embodiments, the CHNFs 1 have superior anti-leaching of clay with three-times higher post-wetting clotting activity compared to QCG. Halloysite clay is also more effective in plasma coagulation than commercial kaolin clay. The physical and thermal properties of the CHNFs were evaluated using scanning electron microscopy, energy dispersive X-ray spectroscopy, X-ray diffraction, Brunauer-Emmett-Teller surface area analysis, and thermogravimetric analysis. In some embodiments, the CHNFs 1 show 7-fold greater clay loading than QCG and their small average diameter of 450 ±260 nm compared to 12.6±0.9 μm for QCG accounts for part of this increase in surface area. This affords a 22-times greater specific surface area (33.6 $m^2 g^{-1}$) than QCG (1.6 $m^2 g^{-1}$).

In some embodiments, the wet-wet electrospinning process relying on a coagulation bath containing the clay suspension, as discussed above, obtained high clay loadings and increased specific surface areas. Fibers electrospun into the clay suspension had 3-fold higher clay loading than when CNFs were simply immersed in halloysite clay suspension to prepare MCNFs. The choice of halloysite nanoclay in place of kaolin clay further enhanced performance. Neat halloysite nanoclay coagulates human plasma approximately 1.6-times faster than neat kaolin clay. Thus, a combination of higher surface area supplied by the electrospun fibers, and enhanced clotting performance of the halloysite nanoclay, increased the overall plasma clotting performance of the CHNFs 1.

In some embodiments, the CHNFs 1 retained over three-times the clotting activity compared with QCG after washing once with water, losing only 24% of its clotting activity compared to a 75% loss of procoagulant activity observed for QCG. This stability of CHNFs 1 is extremely important for stopping traumatic external hemorrhages on the battlefield and in the operating room since continuous blood flow greatly reduces the performance of QCG. When QCG was subjected to washing in distilled water, nearly 80% of its clay content was quickly lost. In some embodiments, the intermediate hydrogel state formed in the coagulation bath during the wet-wet electrospinning process facilitates kinetic entrapment of halloysite nanoclay particles, resulting in higher clay retention of the CHNFs 1. This physical embedding of nanoclay particles during the electrospinning process does not occur with simple immersion of prefabricated CNFs in a clay suspension, which is the process used to produce QCG.

Figure 10:
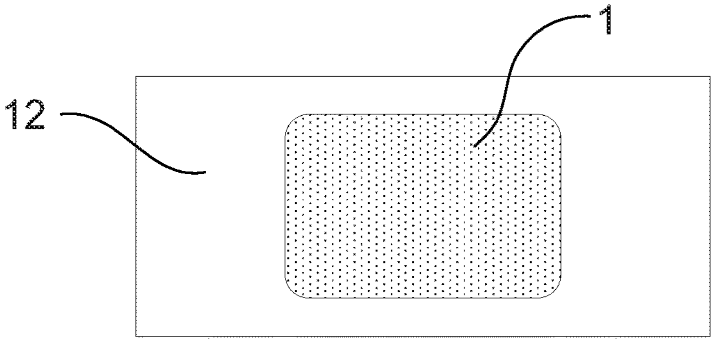
FIG. 10 is a plan view of a hemorrhage-treatment article according to an embodiment of the present technology.

In some embodiments, a CHNF 1 made according to the wet-wet electrospinning process discussed above is used as an anti-hemorrhagic agent. In some embodiments, CHNF 1 is placed on or within a hemorrhage-treatment article 12, as shown in FIG. 10. The hemorrhage-treatment article 12 is used to apply the CHNF 1 to a hemorrhage to coagulate the plasma in animal blood, preferably mammal blood, and more preferably human blood. In some embodiments, the hemorrhage-treatment article 12 is designed for external, topical use, such as a wipe, pad, gauze, bandage, wrap, etc.

Although the technology has been described and illustrated with respect to exemplary embodiments thereof, it should be understood by those skilled in the art that the foregoing and various other changes, omissions, and additions may be made there and thereto, without departing from the spirit and scope of the present technology.

What is claimed is:

1. A method of making a cellulose—nanoclay hemostatic nanocomposite fiber, comprising the steps of:

preparing a cellulose solution including cellulose and a non-volatile solvent;

preparing a first bath comprising a nanoclay suspension that includes an aluminosilicate and water;

electrospinning the cellulose solution into the first bath including the nanoclay suspension to cause precipitation of solidified cellulose-nanoclay fibers;

removing the solidified cellulose—nanoclay fibers from the first bath; and washing the solidified cellulose—nanoclay fibers in a second bath comprising alcohol and water, wherein the aluminosilicate is halloysite, and wherein the solidified cellulose—nanoclay fibers are configured to coagulate human plasma in an average time of about 124 seconds to about 162 seconds.

2. The method of claim 1, wherein the non-volatile solvent is a room temperature ionic liquid.

3. The method of claim 1, wherein the cellulose solution comprises an about 2.12% homogenous cellulose solution.

4. The method of claim 1, wherein the nanoclay suspension further includes alcohol.

5. The method of 1, further comprising the step of:

freeze-drying the solidified cellulose—nanoclay fibers to obtain halloysite clay coated cellulose nanofibers.

6. The method of claim 1, further comprising the steps of:

removing the solidified cellulose—nanoclay fibers from the second bath;

and freeze-drying the solidified cellulose—nanoclay fibers.

7. The method of claim 1, wherein the solidified cellulose—nanoclay fibers have an average diameter of about 190 nm to about 710 nm.

8. The method of claim 1, wherein the solidified cellulose—halloysite fibers have a specific surface area of about 33.6 m2g−1.

9. A cellulose—nanoclay hemostatic nanocomposite fiber made by the method of claim 2.

10. The method of claim 3, wherein the first bath comprises about 10% w/v aluminosilicate.

* * * * *